US012753152B2

(12) United States Patent
O'Keefe

(10) Patent No.: US 12,753,152 B2
(45) Date of Patent: Oct. 6, 2026

(54) METHOD AND APPARATUS FOR THE PRODUCTION OF PERFORMIC ACID

(71) Applicant: SYMBIENT ENVIRONMENTAL TECHNOLOGIES, Missassauga (CA)

(72) Inventor: William Kevin O'Keefe, Georgetown (CA)

(73) Assignee: SYMBIENT ENVIRONMENTAL TECHNOLOGIES, Mississauga (CA)

( * ) Notice: Subject to any disclaimer, the term of this patent is extended or adjusted under 35 U.S.C. 154(b) by 840 days.

(21) Appl. No.: 18/025,773

(22) PCT Filed: Sep. 10, 2021

(86) PCT No.: PCT/CA2021/051253
§ 371 (c)(1),
(2) Date: Mar. 10, 2023

(87) PCT Pub. No.: WO2022/051858
PCT Pub. Date: Mar. 17, 2022

(65) Prior Publication Data

US 2023/0348375 A1 Nov. 2, 2023

Related U.S. Application Data

(60) Provisional application No. 63/211,669, filed on Jun. 17, 2021, provisional application No. 63/076,675, filed on Sep. 10, 2020.

(51) Int. Cl.
*C07C 407/00* (2006.01)
*B01J 23/20* (2006.01)

(52) U.S. Cl.
CPC .......... *C07C 407/003* (2013.01); *B01J 23/20* (2013.01)

(58) Field of Classification Search
None
See application file for complete search history.

(56) References Cited

U.S. PATENT DOCUMENTS 6,049,002 A 4/2000 Mattila et al.
6,211,237 B1 4/2001 Huss et al.
(Continued)

FOREIGN PATENT DOCUMENTS

AU 2018260977 B2 11/2018
AU 2018271409 B2 12/2018
(Continued)

OTHER PUBLICATIONS

Sensorex (downloaded from https://sensorex.com/ion-exchange-and-industrial-applications/?srsltid=AfmBOoogermx3kgkF2RKTiJbg1N666cKNx-cw_ObpSfLEVLJjo_IvVzh On Jan. 22, 2026 (Year: 2026).*
(Continued)

*Primary Examiner* — Amy C Bonaparte

(57) ABSTRACT

A catalytic distillation process, which when operated under vacuum conditions, makes possible the facilitation of peroxyacid chemistry under intrinsically safe conditions with superior efficiency compared to conventional technology. In particular, the process can be used for the production of performic acid (PFA) created from the chemical reaction of formic acid and hydrogen peroxide, while contacting one or more kinds of heterogeneous catalysts, immobilized in one or more regions of the reactor (i.e. within reaction zones within the column). Aqueous hydrogen peroxide and formic acid feed streams are directed to the catalytic distillation column. The products are separated from the reactants in situ from the distillation action within the column The process is made efficient by utilizing moisture tolerant catalyst materials which facilitate the chemical conversion of the reactants operating at or near stoichiometric amount and by (Continued)

operating the catalytic distillation reactor at or near 100% conversion and at an optimal reflux ratio which prevents the accumulation of water in the system while maximizing external mass transfer rates, catalyst wetting efficiency and energy efficiency.

57 Claims, 2 Drawing Sheets

(56) References Cited

U.S. PATENT DOCUMENTS

| | | | | |
|---|---|---|---|---|
| 7,547,421 | B2 | 6/2009 | McSherry | |
| 9,505,715 | B2 | 11/2016 | Kraus et al. | |
| 9,518,013 | B2 | 12/2016 | Li et al. | |
| 9,763,442 | B2 | 9/2017 | Li et al. | |
| 10,172,351 | B2 | 1/2019 | Kraus et al. | |
| 2002/0177732 | A1 | 11/2002 | Pohjanvesi et al. | |
| 2008/0275132 | A1* | 11/2008 | McSherry | C07C 407/00 562/6 |
| 2015/0034566 | A1 | 2/2015 | Karpova et al. | |
| 2016/0137535 | A1 | 5/2016 | Keasler et al. | |
| 2017/0064949 | A1 | 3/2017 | Kraus et al. | |

FOREIGN PATENT DOCUMENTS

| | | | | |
|---|---|---|---|---|
| AU | 2019208211 | B2 | 8/2019 | |
| CN | 105646435 | A | 6/2016 | |
| CN | 110183417 | A | 8/2019 | |
| EP | 0751933 | B1 | 6/1999 | |
| EP | 0974581 | A1 * | 1/2000 | C07C 407/00 |
| EP | 1004576 | A1 | 5/2000 | |
| EP | 1247801 | A1 | 10/2002 | |
| EP | 1931628 | B1 | 11/2010 | |
| EP | 2653448 | A1 | 10/2013 | |
| ES | 2728470 | T3 | 4/2014 | |
| WO | 2014055900 | A1 | 4/2014 | |
| WO | 2017040920 | A1 | 3/2017 | |
| WO | 2021183516 | A1 | 9/2021 | |

OTHER PUBLICATIONS

Translation of Zhou (CN 105646435A, published on Jun. 8, 2016), obtained Jan. 2026 (Year: 2026).*

Krause ("Acidic and basic surface sites of zirconia-based biomass gasification gas clean-up catalysts" Applied Catalysis A: General 362, 2009, p. 169-177) (Year: 2009).*

Boiling (https://www.chem.purdue.edu/gchelp/liquids/boil.html , as captured on Sep. 14, 2001, downloaded from https://web.archive.org/web/20010914160144/https://www.chem.purdue.edu/gchelp/liquids/boil.html on Jan. 22, 2026) (Year: 2001).*

Horsley (Table of Azeotropes and Nonazeotropes, 1947, p. 508 and 516-517). (Year: 1947).*

F. Ebrahimi et al., "Heterogeneously catalyzed synthesis of performic acid in a microstructured reactor", ChE. J., 2012, 179, 312-317.

C.A. Bettenhausen, "How peracetic acid is changing wastewater treatment", Chemical & Engineering News, the American Chemical Society, Apr. 19, 2020, vol. 98, Issue 15, pp. 1-6.

D. Swern, "Organic Peracids", Chem. Rev., 1949, 45, pp. 1-68.

R. Taylor and R. Krishna, "Modelling reactive distillation", Chem. Eng. Sci., 2000, 55, 5183-5229.

K. O'Keefe et al., "Experimental Studies on the Syntheses of Mesityl Oxide and Methyl Isobutyl Ketone via Catalytic Distillation", Ind. Eng. Chem. Res., 2007,46, 716-725.

S. Leveneur et al., "From Kinetic Study to Thermal Safety Assessment: Application to Peroxyformic Acid Synthesis", Ind. Eng. Chem. Res., 2012, 51, 13999-14007.

International Search Report for PCT/CA2021/051253 dated Dec. 16, 2021, 3 pages.

Korvela, Timo. "Zirconium and Some Stainless Steels in Peracetic Acid Production." Kemira Kemi AB, P.O. Box 902, S-25109 Helsingborg, Sweden. Feb. 1997, 8 pages.

ChemSpider, a chemical database managed by the Royal Society of Chemistry 2022, 3 pages.

Tung, S.-T., & Yu, C.-C. (2007). Effects of relative volatility ranking to the design of reactive distillation. AIChE Journal, 53(5), 1278-1297. https://doi.org/10.1002/aic.11168, 20 pages.

* cited by examiner

METHOD AND APPARATUS FOR THE PRODUCTION OF PERFORMIC ACID

CROSS-REFERENCE TO RELATED APPLICATIONS

This application is a National Phase of PCT/CA2021/051253 filed on 10 Sep. 2021, and published on 17 Mar. 2022 as WO 2022/051858, in English, which claims priority to U.S. Provisional Patent Application Nos. 63/076,675 filed on 10 Sep. 2020, and 63/211,669 filed on 17 Jun. 2021, all of which are incorporated herein by reference in their entireties.

FIELD

The present disclosure pertains to the point of use production of disinfectants, in particular performic acid, for use in industrial effluent treatment, wastewater treatment and the disinfection of medical and food processing equipment.

BACKGROUND

Chemical disinfection in wastewater treatment has been traditionally achieved by the introduction of chlorine containing compounds such as sodium hypochlorite and chlorine dioxide. However, residual chlorine and associated disinfection by-products have raised concerns about their effects on human health and the environment, including its effect on aquatic life. Moreover, there is a significant cost associated with the need to neutralize chlorine before discharge of the treated effluent, which is being exacerbated by increasingly strict environmental regulation (see ref 1). Today, chlorine is still used in two thirds of 16,000 waste water treatment plants in the USA.

Peracetic acid (PAA) is a second generation disinfectant, which is now being frequently used in these applications. It is a stronger oxidant than hypochlorite, affording rapid disinfection and its decomposition products are relatively non-toxic, requiring little neutralization. Performic acid (PFA) represents a third generation chemical disinfectant for wastewater treatment. PFA has significant potential advantages in that it is more effective as a disinfectant and is faster acting than PAA or hydrogen peroxide and has been proven to be effective at low temperatures, which is a requirement in wastewater treatment. PFA is also believed to be economically superior to PAA for this purpose. The decomposition products of PFA (water, oxygen and carbon dioxide) are non-toxic and do not require a neutralization stage.

PFA is produced from the reaction of hydrogen peroxide with formic acid (Equation 1). The conventional technology is a batch process whereby aqueous solutions of formic acid and hydrogen peroxide are mixed in the presence of a homogeneous mineral acid catalyst such as sulfuric acid, nitric acid, phosphoric acid or other strong acids to produce an aqueous mixture containing PFA and the reactants. A significant disadvantage of the conventional technology is that the reaction is equilibrium limited. That is, there is a maximum possible attainable yield due to thermodynamic constraints. For example, EP12164979 and US20150034566A1 describe the state of the art production of PFA whereby formic acid is combined with hydrogen peroxide in the presence of a sulphuric acid catalyst to produce an equilibrium mixture of PFA, denoted by the tradename Kemira DEX-135, which is comprised of 13.5 (w/v) % PFA (i.e. 13.5 g of PFA per 100 mL), (see refs. 2, 3).

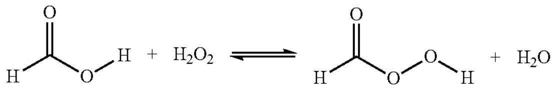

(1)

To maximize the yield and reduce the reaction time, in practice, the concentration of reactants are maximized, which is hazardous and can result in the release of a significant amount of energy due to the exothermic nature of the chemical reaction. PFA, being highly oxygenated is an energetic molecule that can explode upon heating over 80° C. (see ref. 4). The use of high concentration of reactants in the presence of a significant amount of strong mineral acid catalyst results improves the space time requirements, but is hazardous and also results in undesirable consecutive reactions such as the decomposition of PFA, which further reduces the process yield. For example, Ebrahimi et al. found that in the presence of a strong sulfuric acid catalyst, consecutive reactions resulting in the decomposition of PFA were significant and became dominant above 40° C. (see ref. 5). This is an issue with the conventional technology where the reaction is conducted in a closed system with significant energy release associated with the chemical reaction, which can cause the system temperature to rise abruptly.

The use of strong liquid acids can also introduce corrosion issues. Aksela and Mattila (EP0751933B1) describe the use of a homogeneous catalyst comprised of a compound containing at least one ester group, and or another functional group differing from a carboxylic acid group and an alcohol group, preferably a carboxylic acid ester, (see ref. 6). However, liquid catalysts like this will also become consumed in the product effluent resulting in the catalytic reagent becoming a consumable, contributing to the overall cost. Moreover, the presence of residual catalyst in the product effluent can facilitate continued and undesired consecutive reactions, thereby reducing the process yield.

A significant disadvantage of the use of PFA is its instability. PFA must be used within 12 hours of its manufacture. Some approaches include the use of stabilizers to the equilibrium mixtures containing percarboxilic acids such as described by Li et al (US20160137535A1, ES2728470T3), (see refs. 7, 8). Some known stabilizers for performic acid include phosphonic acid and phosphonate salts including HEDP, ethylenediamine tetrakis methylenephosphonic acid, cyclohexane-1,2-tetramethylene phosphonic acid, amino [tri (methylene phosphonic acid)], ethylene diamine[tetramethylene-phosphonic acid)] 2-phosphene butane-1,2,4 tricarboxylic acid, alkali metal salts, ammonium salts, alkyloyl amine salts picolinic acid, dipicolinic acid and so on. Thus the use of equilibrium mixtures is often associated with the additional cost due to the use of stabilizers.

Point of use systems whereby PFA is produced on site at the location where it is to be utilized are advantageous. Balasubramanian et al. (AU2019208211A, US20170064949A1) describes a system and apparatus of contacting an aqueous formic acid with an oxidizing agent in the liquid phase in a continuous flow reactor, (see refs. 9, 10). The inventors note that the use of a liquid mineral acid catalyst can cause corrosion issues in downstream piping and propose the generation of PFA in the flow reactor using heat only to facilitate the chemical reaction. The flow reactor is a pipe whereby the reactants, formic acid and hydrogen peroxide, are introduced into the aqueous influent entering the pipe, preferably under conditions of laminar flow, which is heated by a cartridge heater for example to facilitate the chemical reaction and whereby the product effluent stream is cooled to a temperature at or below freezing. This approach however has the distinct disadvantage of being energy intensive, by not utilizing a catalyst to facilitate the chemistry and from the requirement of energy addition to the system to drive the reaction followed by the subsequent removal of energy when cooling the effluent. Moreover, the chemistry is not well controlled without the use of a catalyst. The inventors make the dubious assertion that performic acid concentrations in excess of the equilibrium concentration can be achieved; that is, the conversion of the reaction is not equilibrium limited, which the inventors attribute due to the reaction being conducted stoichiometrically, in situ in an open system; which runs contrary to fundamental principles of chemical reaction engineering. The inventors suggest the reaction can be run at temperatures up to 180° C. but not exceeding 200° C. This is potentially dangerous due to the explosive nature of PFA when heated and likely to be inefficient given the known instability of PFA. The inventors suggest construction of the reactor using steel to have a high burst strength and the system engineered to ensure the pressure does not exceed the burst strength.

Kraus et al. (U.S. Pat. No. 950,571B2) describe an onsite generator for peroxycarboxylic acids can be generated from sugar esters in a batch system, using one or more reaction vessels, where the reagents including polyhydric alcohol and C1 carboxylic acid are combined with an oxidizing agent in the presence of a source of alkalinity (i.e. a homogeneous basic catalyst) in the form of dissolved sodium hydroxide (see ref. 11). This process affords the flexibility of changing the composition of the product by varying the composition of the feed stream, however it has the aforementioned limitations of conventional technology, including being constrained by the thermodynamic equilibrium limitation on the chemical conversion and requiring significant homogeneous catalyst consumption required to facilitate the chemistry. The inventors suggest up to 20 wt % sodium hydroxide may be required in the reactor. In a similar disclosure, inventors from the same company disclose the production of PFA from mixtures of a reagent containing formic acid and polyhydric alcohol a second reagent containing hydrogen peroxide or forming hydrogen peroxide in situ (see ref. 12). In one embodiment, the second reagent is in solid form, creating hydrogen peroxide on demand when dissolved for use.

SUMMARY

The present disclosure provides a catalytic distillation process, which when operated under vacuum conditions, makes possible the facilitation of peroxyacid chemistry under intrinsically safe conditions with superior efficiency compared to conventional technology. The process can be used for the production of performic acid (PFA) created from the chemical reaction of formic acid and hydrogen peroxide, while contacting one or more kinds of heterogeneous catalysts, immobilized in one or more regions of the reactor (i.e. within reaction zones within the column). Aqueous hydrogen peroxide and formic acid feed streams are directed to the catalytic distillation column and the reaction products are separated from the reactants in situ, from the distillation action within the column. PFA, which, based on its boing point of 127.5° C. at 760 mm Hg reported in Chemspider (Ref. 13), would be the least volatile constituent and becomes concentrated in the bottoms product stream, while unreacted formic acid, $H_2O_2$ and water can be extracted in the overhead distillate. The process is made efficient by utilizing moisture tolerant catalyst materials which facilitate the chemical conversion of the reactants operating at or near stoichiometric amount and by operating the distillation reactor at or near 100% conversion and at an optimal reflux ratio which prevents the accumulation of water in the system.

However, there is some ambiguity in the science. Due to its reactivity, the boiling point of PFA cannot be measured directly. The boiling point of PFA in Chemspider is based on molecular modelling. However, it can be seen from trends of boiling points of peracids which can be measured experimentally, when contrasted to the boiling points of their parent acids, that the peracids consistently have lower boiling points than their corresponding parent acids. For example, acetic acid has a normal boiling point of 118° C., while peracetic acid has a normal boiling point of 105° C. Consequently, based on this trend, the boiling point of PFA may be expected to be less than its parent acid, formic acid, which has a normal boiling point of 101° C. Therefore, a second embodiment is disclosed herein, whereby PFA is the most volatile compound and becomes concentrated in the overhead distillate product, while unreacted formic acid and hydrogen peroxide concentrate in the reboiler and a proportion of the bottoms product may be recycled to the CD reactor while the remainder may be drawn from the reactor to purge the system.

Thus, the present disclosure provides a catalytic distillation process for the production of performic acid, comprising feeding aqueous solutions of formic acid and an oxidizing agent under controlled flow rates into a catalytic distillation column containing or more reaction zones located generally in the middle of the column, with the one or more reaction zones including one or more heterogeneous catalysts immobilized in the one or more reaction zones. The column is operated at a pressure ranging from sub-atmospheric pressure to slightly above atmospheric pressure to obtain a predetermined temperature such that the oxidizing agent and formic acid mix in the one or more reaction zones and undergo a reaction to produce PFA and reaction by-products. It would be known to one skilled in the art that the predetermined temperature should be less than 40° C. to ensure a high yield of PFA and to ensure the safe operation of the process equipment due to the reactive nature of PFA and the oxygenated reactants. Thus, the catalytic distillation process should be run under atmospheric conditions, with a vacuum pressure typically less than −26 in Hg. The PFA product is recovered, either from the bottoms product (first embodiment) or the overhead distillate (second embodiment), while the unreacted formic acid and oxidizing agents may be recycled to the reactor in some proportion either by reflux from the condenser (first embodiment) or by controlling the purge rate from the reboiler (second embodiment). Due to its low stability, the PFA rich aqueous product is typically consumed for its intended purpose after production by the CD process, however, it may be cooled and stored for some period.

The pressure may be in a range from about $1\times10^{-6}$ psia to about 14.7 psia.

The pressure may be in a range from about 0.1 psia to about 3 psia.

The pressure may be in a range from about 0.3 to about 1.1 psia.

The preselected temperature in the reaction zone containing the catalyst may be in a range from about 0 to 100° C.

The preselected temperature in the reaction zone containing the catalyst may be in a range from about 15° C. to about 60° C.

The preselected temperature in the reaction zone containing the catalyst may be in a range from about 20° C. to about 40° C.

The oxidizing agent may be hydrogen peroxide such that the hydrogen peroxide and formic acid mix in the one or more reaction zones and undergo the reaction (1) to produce performic acid and water as a reaction by-product as follows:

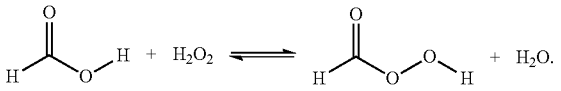

(1)

The oxidizing agent may be a compound which can produce hydrogen peroxide in situ via its chemical reaction with other compounds present in the system or by interaction with the catalyst in the system.

The heterogeneous catalyst may be a cation exchange resin and this cation exchange resin may be any one of Amberlyst® 15; DIONEX™ SK, PK and HPK series or acid functionalized variants of DIONEX™ including weakly acidic methacrylic or acrylic type ion exchange resins; SEPLITE® MC and LPF series and acid functionalized variants of SEPLITE® cation exchange resins, Purolite® cation exchange resins and their acid functionalized variants; Nafion™ HP, Dowex®-50 series, Dowex® NCR series, Dowex® MARATHON™ MR3, Dowex® MARATHON™ CH and any acid functionalized variants of Dowex® resins; Amberlite IRC83H and other acid functionalized variants of Amberlite™ resins.

The heterogeneous catalyst may be a transition metal oxide.

The heterogeneous catalyst may comprise at least one metal oxide exhibiting either Bronsted or Lewis acidity, or exhibits amphoteric properties.

The heterogeneous catalyst may comprise at least one metal oxide selected from the group $Nb_2O_5$, $Al_2O_3$, $ZrO_2$, $TiO_2$, $Cr_2O_3$, $CrO_3$, $WO_3$, $W_2O_5$, $ZrW_xO_y$ (wherein x is 2 and y is 0.5 to 8), $V_2O_5$, BeO, $MoO_3$, $Fe_2O_3$, $Ga_2O_3$, $La_2O_3$, ZnO and mixtures thereof.

The heterogeneous catalyst may contain a transition metal oxide with a transition metal selected from the group consisting of Fe, Ti, Zr, Hf, Sn and Si and Al and combinations thereof, and wherein the metal oxide has been treated by an acidic material.

The acidic material may be selected from the group consisting of $SO_4/SnO_2$, $SO_4/ZrO_2$, $SO_4/HfO_2$, $SO_4/TiO_2$, $SO_4/Al_2O_3$, $SO_4/Fe_2O_3$, $MoO_3/ZrO_2$, $SO_4/SiO_2$, $WO_3/SrO_2$, $WO_3$, $TiO_2$, $WO_3/Fe_2O_3$, $B_2O_3/ZrO_2$ and combinations thereof.

The heterogeneous catalyst may be a water insoluble basic catalyst.

The heterogeneous catalyst may be an amphoteric material exhibiting basic sites. The amphoteric material exhibiting basic sites may include any one or combination of MgO, CeO2, Al2O3, Fe2O3, Cr2O3 or a basic anion exchange resin for example such as Amberlite™ IRA 900, DIAION™ (Mitsubishi).

The aqueous solutions of formic acid and the oxidizing agent may be mixed together and then fed into the catalytic distillation column, or more generally fed separately at locations which optimize the process.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

The Figures may not be to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

A goal of the process disclosed herein is to obviate or mitigate at least one of the above-mentioned disadvantages of the prior art and to provide a novel element that obviates or mitigates at least one of the above-mentioned disadvantages of the prior art.

Figure 1:
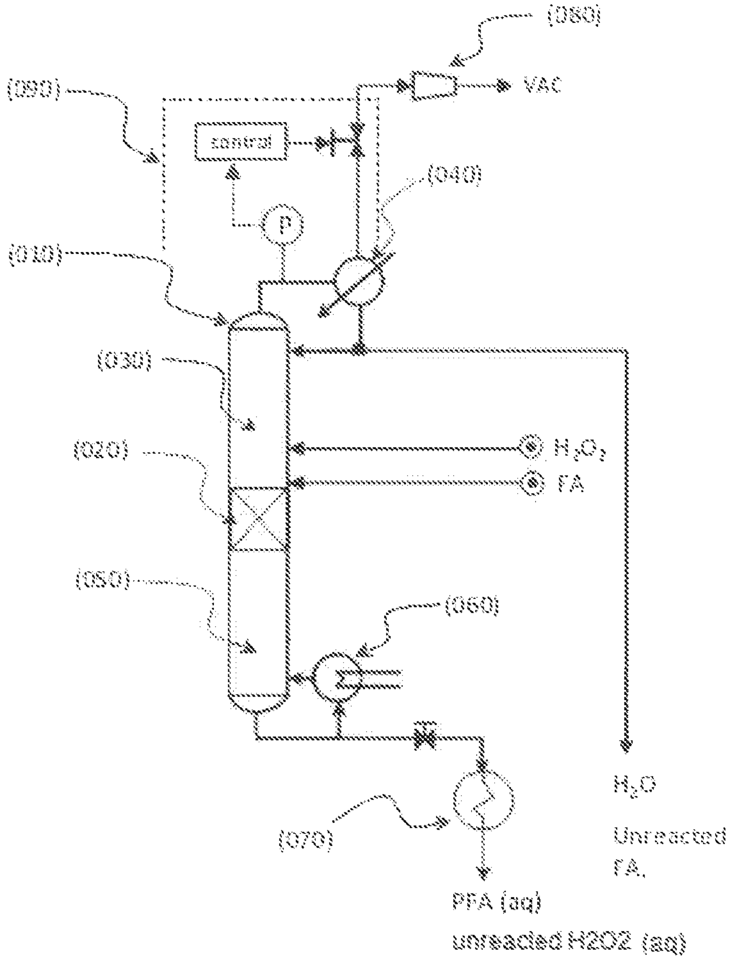
FIG. 1 shows a schematic representation of a first embodiment a catalytic distillation process for the production of performic acid (PFA) and water ($H_2O$) from hydrogen peroxide ($H_2O_2$) and formic acid (FA).
Figure 2:
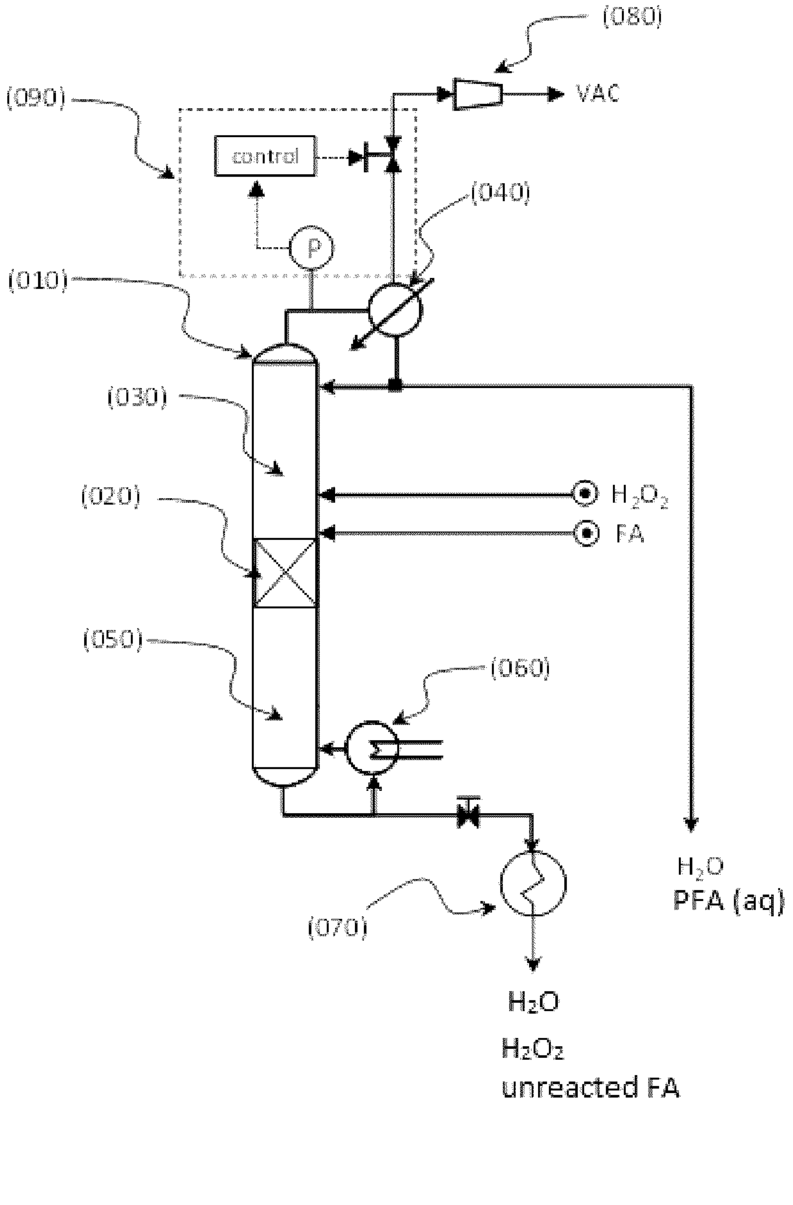
FIG. 2 shows a schematic representation of a second embodiment of a catalytic distillation process for the production of performic acid (PFA) and water ($H_2O$) from hydrogen peroxide ($H_2O_2$) and formic acid (FA).

Accordingly, the present disclosure provides a novel catalytic distillation process for the point of use production of PFA in high yield with the first embodiment as outlined in FIG. 1 and the second embodiment as outlined in FIG. 2. The reactor in FIG. 1 is a catalytic distillation reactor system, the concept of which is known to those skilled in the art. The reactor internals are comprised of either distillation media (packing) or trays depending on the scale of the process. Heterogeneous catalyst is immobilized in one or more reaction zones (020) within the column (010) in a manner known to those skilled in the art, for example as described by Taylor and Krishna (*Chem. Eng. Sci.,* 2000, 55, 5183), such as in the form of catalyst pellets or extrudate, catalyst material retained within structured porous tubes, envelopes and structured packings, such as KATAPAK®-S (Sulzer Chemtech) or KATAMAX® (Koch-Glitsch), or within catalytic coatings deposited onto reactor internals or media. Reactants are continuously fed to the reactor system. In the case of the first embodiment shown in FIG. 1, aqueous solutions of hydrogen peroxide ($H_2O_2$) and formic acid (FA) are fed to the reactor separately and a PFA rich product stream is drawn from the bottoms product. In the case of the second embodiment shown in FIG. 2, the PFA rich product stream is drawn from the overhead distillate.

FIG. 1 illustrates the process flow for a catalytic distillation process for the production of PFA from formic acid (FA) and hydrogen peroxide. The catalytic distillation column (CD) (010) is comprised of 3 main sections. A reaction zone (020) which contains the immobilized catalyst noted above, a rectification section (030) located above the reaction zone (020) and a stripping section (050) located below the reaction zone (020). The stripping and rectification sections (050) and (030) do not contain catalyst but do contain distillation media such as Pall rings, Raschig rings or if the column (010) is sufficiently large, may contain other internals to promote heat and mass transfer such as sieve trays. Aqueous hydrogen peroxide and FA are fed to the catalytic distillation column separately at controlled flow rates. Without loss of generality, the embodiments of the systems and processes shown in FIGS. 1 and 2 show the feed streams of FA and $H_2O_2$ located near the reaction zone (020) for illustrative purpose. The precise locations can be chosen to optimize the outcome of the process. Within the CD column (010), liquid flows downward under the influence of gravity under conditions of trickle flow wetting and spreading over the distillation media and immobilized solid catalyst.

A vapour phase rises in the column and is condensed in the condenser (040). As the vapour rises in the column (010), the vapour phase becomes more concentrated with the volatile fractions in the rectification section (030); liquid that falls in the column (010) becomes increasingly enriched in the less volatile fractions. A reboiler (060) at the bottom of the column provides the energy to drive the distillation process, causing the product at the bottom of the column (010) to maintain a boiling condition.

A bottoms product can be recovered from the bottom of the column (010) and rapidly cooled with a heat exchanger (070). Similarly, an overhead distillate product stream can be drawn from the top of the column (010). Due to the ambiguity in the literature regarding the boiling point of PFA, two embodiments have been presented. In the first embodiment (FIG. 1), the PFA rich stream is recovered in the bottoms product, while in the second embodiment (FIG. 2), the PFA rich stream is produced in the overhead distillate. However, a proportion of the condensed distillate is refluxed to the catalytic distillation column. A vacuum pump (080) and control system (090) can be employed to control the pressure in the column (010), reducing it to sub atmospheric pressure by connection with the distillate head at the top of the column (010).

The process for production of performic acid using the apparatus of FIGS. 1 and 2 will now be described but it will be appreciated this method is exemplary and non-limiting. It will be understood that, the precise location of feed streams can be selected to optimize the process conditions and that a multiplicity of catalysts and reaction zones (020) may be employed. Within the column (010), a boiling liquid falls under the influence of gravity, in the low interaction regime of trickle flow wetting and spreading over the distillation media while a vapour phase rises in a counter-current fashion towards the top of the column (010). The presence of sieve trays or distillation media promote mass and heat transfer between these phases. When in the reaction zones (020) of the column (010), liquid and vapour phases contact the catalyst which facilitates the chemical conversion of formic acid and hydrogen peroxide to water and PFA.

The more volatile components rise towards the top of the column, becoming more concentrated in the rectification section (030) and most concentrated in the overhead distillate leaving the condenser (040). A proportion of the distillate stream is returned to the column as reflux, while some of this stream may be drawn from the reactor as a distillate product. In the first embodiment (FIG. 1) PFA, is presumed to be less volatile, and will become more concentrated in the stripping section (050) of the column and most concentrated reboiler (060) from which the bottoms product is drawn. The bottoms product can be cooled using a heat exchanger (070). In the second embodiment (FIG. 2) PFA is presumed to be more volatile and therefore become more concentrated in the overhead distillate, producing a PFA rich product stream. Thus, a continuous and concentrated PFA rich stream can be produced for on site, point of use generation as a disinfectant. The concentration of PFA in the bottoms or distillate product streams and the rate of its production can be controlled by the mass flow rate of reactants as well as by adjusting the reflux ratio of the catalytic distillation reactor as well as the product mass flow rates including the distillate and bottoms product streams.

Formic acid has a normal boiling point of 100.8° C. Although the normal boiling point of hydrogen peroxide is 150° C., in aqueous systems, water will form non-ideal mixtures with hydrogen peroxide, due to hydrogen bonding, resulting in bubble points which range from 105 to 114° C., for mixtures ranging from 27 to 50 wt % $H_2O_2$ respectively. The normal boiling point of PFA cannot be measured experimentally but has been estimated to be 127.5±23° C. based on numerical calculations (see ref. 13). Thus, PFA appears to be significantly less volatile than the reactants (formic acid and hydrogen peroxide) and the other by-product (water), which suggests separation of PFA from the reactants by distillation is possible. In the first embodiment (FIG. 1) it is assumed due to its low volatility, that PFA will substantially concentrate in the reboiler creating a PFA rich bottoms product stream and be present to a much lesser extent or not at all in the overhead distillate stream. Since the bubble point of a $H_2O_2/H_2O$ mixture increases with increasing concentration of $H_2O_2$, the current inventors realized that the efficacy of the separation of PFA from the mixture, (if PFA is presumed to have a normal boiling point of 127° C.), via catalytic distillation can be improved by operating the reactor under conditions where the catalytic conversion of $H_2O_2$ is close to 100%, by using $H_2O_2$ either as the limiting reagent or in stochiometric amount with formic acid or not significantly in stoichiometric excess of the formic acid and by operating the reactor at sufficiently low space velocity to ensure the catalytic conversion of hydrogen peroxide is close to 100%. Thus, the relative volatility of PFA and the remaining constituents will be sufficiently high to affect its purification by distillation.

Although the boiling point of PFA has been estimated to be 127° C. by computational methods, this contradicts the boiling point trends observed for peracids of experimentally verified boiling points whereby the boiling point of the peracid is typically lower than the parent acid. Based on these observations, a second embodiment (FIG. 2) is contemplated by the inventors where the boiling point of PFA is less than FA, and therefore is the most volatile constituent in the process and will substantially concentrate in the overhead distillate stream and to a much lesser extent or not at all in the bottoms product stream.

Thus, it will be appreciated that in the embodiment of FIG. 1, the majority of the PFA is taken from the bottom of the column there may be smaller amounts of PFA in the top of the column and the same goes for the embodiment of FIG. 2, the majority of the product is taken from the top of the column but there may be smaller amounts located in the bottom of the column.

In a catalytic distillation process, there are insufficient degrees of freedom to independently specify temperature and pressure. The boiling point of the mixture depends on its composition and the system pressure. Since the composition of the liquid changes throughout the column, there is a temperature gradient in the column being a maximum in the reboiler at the bottom of the column and a minimum at the condenser at the top of the column. Due to the energetic and unstable nature of PFA, operating a catalytic distillation reactor at a temperature near the normal boiling point of water to produce a concentrated boiling PFA product near the normal boiling point of PFA is neither technically feasible nor advisable for producing concentrated solutions of PFA. However, the current inventors discovered that by operating the catalytic distillation column under sub atmospheric conditions by connecting a vacuum pump (100) to the distillate head at the condenser to reduce the overall system pressure to a range from about 27 to about 29 in Hg, the temperature in the reaction zone can be reduced to temperatures below 40° C., providing advantageous conditions to facilitate the production of PFA while minimizing undesirable consecutive reactions, such as the decomposition of PFA into carbon dioxide. Similarly, the PFA product, can be maintained at a relatively low temperature and (optionally) rapidly quenched by a heat exchanger when drawn from the reactor.

Solid acid catalysts exhibiting either Bronsted and or Lewis acid sites can be immobilized in the reaction zone, in a manner as described previously and known to those skilled in the art, and used to facilitate the production of PFA from formic acid and hydrogen peroxide. Acidic cation exchange resins, such as Amberlyst® 15 and other cation exchange resins could be used to catalyze the reaction (see ref. 14). Other particularly useful catalysts include $Nb_2O_5/X$ where X denotes a ceramic catalyst carrier substrate such as a metal oxide like $SiO_2$, $Al_2O_3$, and so on. Generally, solid acid catalysts described by Tanabe can potentially be used to affect the catalytic conversion of formic acid and hydrogen peroxide to PFA and water (see ref. 15). Some reactions that are solid acid catalyzed, can also be catalyzed by solid basic catalysts although the fundamental reaction mechanisms will be different. However, from an industrial perspective, acid catalysts are typically more robust and preferred.

The use of an immobilized heterogeneous catalyst offers significant advantages over the use of homogeneous catalysts described previously in the prior art. For example, the use of liquid mineral acid catalysts like sulphuric acid can cause corrosion issues to equipment and piping. In addition, the homogeneous acid catalysts are residual in the product and can destabilize PFA accelerating its degradation to oxygen, carbon dioxide and water unless neutralized. The use of homogeneous acid catalysts requires that the catalyst be a consumable reagent as separation and recovery of the homogeneous catalyst would not be economically viable. In contrast, solid catalysts (heterogeneous catalysts) immobilized in a reactor are fixed in place and not be residual in the product. The rapid separation of the product stream from the catalyst reaction significantly minimizes undesirable consecutive reactions and obviates the need for neutralization of the product stream or recovery of the homogeneous catalyst.

The solid catalyst used in the catalytic distillation process does not become consumed or lost in the product stream, which is a distinct advantage over the conventional technology. Heterogeneous catalysts may be regenerated in place after some period of operation to restore its functionality. Eventually, heterogeneous catalysts are replaced, typically after several years. It has been reported that the continuous distillation action in a catalytic distillation process, helps reduce catalyst poisoning, thereby greatly extending the viable catalyst life (see ref. 16).

A significant advantage and the distinguishing feature of catalytic distillation, from which it gains its greatest utility is the ability to simultaneously conduct chemical reaction and product purification in a single unit operation. The continuous removal of product from the reaction zone by the distillation action, keeps the product concentration at the boundary layer near the catalyst surface very low compared to the very high reactant concentration. This is known to shift the chemical equilibrium in favour of product formation in accordance with Le Chatêliers Principle circumventing the thermodynamic equilibrium conversion constraint. It has been proven experimentally and is known to those skilled in the art, that chemical conversions as high as 100% for otherwise equilibrium limited reactions can be achieved using catalytic distillation (see refs. 17, 18). Thus, the use of catalytic distillation to produce PFA will enable product yield in excess of the theoretical equilibrium conversion, which is a distinct advantage over the conventional technology described in the prior art. The rapid removal of products from the reactant zone is also known to greatly minimize the occurrence of undesirable consecutive reactions, such as the decomposition of PFA and result in a concentrated PFA product whose concentration is adjustable as desired by the operator of the process.

The strongly exothermic reaction associated with PFA production as well as the instability of PFA are significant challenges for conventional technology. The proposed process disclosed herein, using catalytic distillation, offers a unique advantage in this regard. Since the reaction occurs in a boiling medium, the reaction temperature will remain constant, providing more precise control over the chemical reaction. All of the reaction heat generated is efficiently converted to drive the distillation process and thereby reduce energy consumption requirements. Furthermore, heat transfer efficiency is maximized in a boiling medium. The fact that the heat of reaction is absorbed by the boiling liquid provides a significant advantage in terms of safety, since the temperature of a boiling liquid will not increase further due to the addition of energy.

Thus, hot spot formation and thermal runaway chemical reactions can be prevented in the instance of a significant exotherm or other unexpectedly large release of energy in the system. This is particularly advantageous for the production of energetic and highly oxygenated species like peracid compounds, including PFA. In fact, the potential for runaway reactions has been identified as a significant safety risk for the conventional technology used to produce PFA, wherein PFA is produced in a batch or semi-batch reactor; Leveneur et al. (Ref. 19) conducted a thermal safety assessment of the production of PFA using a semi-batch reactor and advise that the criticality of the reaction is class 5 based on Stoessel classification and that a continuous flow system is recommended instead of a batch system for industrial production. Thus, the proposed invention using catalytic distillation technology obviates this critical deficiency of the state of the art by providing a continuous flow system and by mitigating the potential for hot spots and thermal runaway by conducting the reaction in a boiling medium.

Preferred Embodiments of the Process

The sizing of the reactor including the amount of catalyst required in the catalyst zones is dependent on the production requirements including the required throughput, the concentration of PFA in the desired product stream and the nature of the catalyst selected for the process.

The reaction temperature will be governed by the system pressure. The ideal reaction temperature is dependent on the nature of the catalyst used which governs the reaction kinetics. The operator designs and configures the process to ensure excessive temperatures are not achieved and that excessive concentrations are not achieved which can create potentially explosive or detonable mixtures, depending on the desired concentration of PFA in the PFA rich product stream. The catalytic distillation process should be carried out at a system pressure ranging from about 0.1 to about 14.7 psia. More preferably, the catalytic distillation should be carried out at a system pressure ranging from about 0.1 to about 3 psia. Most preferably, the catalytic distillation process should be carried out at a system pressure ranging from about 0.3 to about 1.1 psia.

Due to the ambiguity in the science regarding the boiling point of PFA, two process embodiments are disclosed. In the first embodiment (FIG. 1), an overhead distillate stream may optionally be drawn to facilitate the removal of water from the system to prevent its accumulation. The reflux ratio is defined as the mass of distillate returned to the column to the mass of distillate recovered as an overhead product. The column may be operated at total reflux (i.e. 100% of distillate returned to the column). More preferably, the column may be operated at a reflux ratio ranging from 20% to 99.9% (distillate returned to the column) and most preferably the column may be operated at a reflux ratio ranging from 90% to 99%.

In the second embodiment (FIG. 2), which presumes that PFA is the most volatile compound, a PFA rich overhead distillate product can be recovered while some proportion of the PFA rich distillate is returned to the CD column as reflux. A bottoms product may be drawn. The reflux rate of the overhead distillate may be optimized to ensure maximum energy efficiency while achieving the target PFA production rates and concentrations as well as target liquid flow rates within the column to ensure adequate catalyst wetting efficiency and promote mass and heat transfer. The reflux rate may range from 0% (no reflux) to 99.9% (returned to column). More preferably, the reflux rate may range from 20 to 97%, most preferably the reflux rate ranges from 50 to 90%.

The catalyst is preferably a solid having significant surface acidity preferably with a Hammet acidity ($H_0$) less than 0. The catalyst used should be a strongly acidic cation exchange resin, preferably Amberlyst-15. Most preferably the catalyst is a moisture tolerant $Nb_2O_5/SiO_2$ catalyst, either provided in the form of a catalytic coating applied directly onto distillation media or more having the $Nb_2O_5$ grafted onto a $SiO_2$ carrier shaped in the form of a distillation packing, like a Raschig ring and whereby the $Nb_2O_5$ has strong Bronsted acidity and its loading is equivalent to one monolayer coverage on the $SiO_2$ catalyst carrier.

While PFA is unstable and is typically used in situ provided by a point of use generator on site, it is not typically stored. It spontaneously decomposes usually over 12 h, but storage in a surge tank containing the PFA product is possible to ensure continuous provision of the PFA rich stream to the end use application during temporary process disruptions.

The reactor is operated in a manner which ensures that hydrogen peroxide ($H_2O_2$) is not in substantial stoichiometric excess of formic acid (FA). The stoichiometric ratio of $H_2O_2$:FA can range from about 100 to about 1. More preferably, the stoichiometric ratio of $H_2O_2$:FA can range from about 2 to about 1, most preferably the stoichiometric ratio of $H_2O_2$:FA should range from about 1.20 to about 1.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. C. A. Bettenhausen, Chemical & Engineering News, the American Chemical Society, Apr. 19, 2020, Vol. 98, Issue 15.
2. T. Karpova, E. Melin, A. Vuori, U. Ojstedt, R. Gramstad, K. Jansson, M. Kolari; (2013) "Water Treatment", US20150034566A1.
3. U. Ojstedt, R. Gramstad, K. Jansson, M. Kolari (2012), "Water Treatment", EP12164979.
4. D. Swern, *Chem. Rev.,* 1949, 45, 1.
5. F Ebrahimi et al., *Chem. Eng. J.,* 2012, 179, 312.
6. T. Aksela and T. Mattilia, "A method for the preparation of aqueous solutions containing performic acid as well as their use", EP0751933B1.
7. V. Kessler, R. De Paula, J. Li, D. McSherry, B. Herdt, R. Staub and R. Ryther (2013), US20160137535A1.
8. J. Li, D. McSherry, A. Brewster, R. Staub, P. De, J. Bolduc, R. Ryther, V. Kessler, "Stable compositions of percarboxylic acid and uses thereof", ES2728470T3.
9. R. Balasubramanian, J. Breshears, B. Brunner, B. Crew, C. Hanson, A. Kleczewski, R. Kraus, J. LI, D. McSherry, R. Staub, M. Tran and I. Yunus, "Performic Acid on-site Generator and Formulator", AU2019208211B2.

10. P. Kraus, B. Crew, J. Li, D. McSherry, R. Balasubramanian, R. Staub, A Kleczewski, M. Tran, C. Hanson, I. Yunus, J. Bresearhs, B. Brunner, "Performic acid on-site generator and formulator" US20170064949A1.

11. P. Kraus, R. Mehus, K. Sanville and T. Rustard, "Sugar ester peracid onsite generator and formulator", US95057152B.

12. A. Brewster, T Cheritu, J. Fast, C. Hanson, S. Lange, J. Li and R. Staub "Generation of peroxyformic acid through polyhydric alcohol formate", AU2018271409B2.

13. B. Elves et al. (Ed.) (1991) *Ullman's Encyclopedia of Industrial Chemistry*, $5^{th}$ Ed. (Wiley), pg. 206.

14. F Ebrahimi et al., Chem. Eng. J., 2012, 179, 312.

15. K. Tanabe, *Solid Acids and Bases: Their Catalytic Properties*, Elsevier (2012).

16. K. Rock, T. McGuirk and G. Gildert, *Chemical Engineering*, 1997, 104, 7.

17. R. Taylor and R. Krishna, *Chem. Eng. Sci.*, 2000, 55, 5183.

18. K. O'Keefe et al., *Ind. Eng. Chem. Res.*, 2007, 46, 716.

19. S. Leveneur et al., *Ind. Eng. Chem. Res.*, 2012, 51, 13999.

Therefore what is claimed is:

1. A catalytic distillation process for production of performic acid, comprising:

feeding aqueous solutions of formic acid and an oxidizing agent under controlled flow rates into a catalytic distillation column containing one or more reaction zones, said one or more reaction zones including one or more heterogeneous catalysts immobilized in said one or more reaction zones, where said one or more heterogeneous catalysts are solid acid catalysts with a Hammet acidity ($H_0$) less than 0;

said column being operated at sub atmospheric pressure and preselected temperature such that the oxidizing agent and formic acid are introduced to the one or more reaction zones and undergo a reaction to produce performic acid and reaction by-products;

wherein a performic acid enriched liquid product containing some unreacted oxidizing agent flows downwards within the column and wherein a vapor phase containing unreacted formic acid, some unreacted oxidizing agent and reaction products rise up within the column to a condenser located at the top of the column; and withdrawing the vapor phase containing the unreacted formic acid, some unreacted oxidizing agent and reaction products from a condenser located at the top of the column, and returning some or all of the condensed distillate back to the CD column as reflux, and withdrawing the performic acid enriched liquid product at or near the bottom of the column to create a performic acid rich bottoms product stream, optionally cooling the performic acid rich bottoms product stream and optionally storing the cooled performic acid rich bottoms product stream.

2. The catalytic distillation process according to claim 1, wherein the preselected temperature is in a range from about 0 to about 100° C.

3. The catalytic distillation process according to claim 1, wherein the preselected temperature in the one or more reaction zones containing the catalyst is in a range from about 15° C. to about 60° C.

4. The catalytic distillation process according to claim 1, wherein the preselected temperature in the one or more reaction zones containing the catalyst is in a range from about 20° C. to about 40° C.

5. The catalytic distillation process according to claim 1, wherein the oxidizing agent is hydrogen peroxide such that the hydrogen peroxide and formic acid mix in the one or more reaction zones and undergo the reaction (1) to produce performic acid and water as a reaction by product as follows

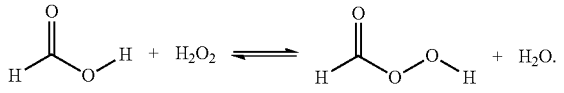

(1)

6. The catalytic distillation process according to claims claim 1, wherein the oxidizing agent is a compound which can produce hydrogen peroxide in situ via its chemical reaction with other compounds present in the system from its interaction with the catalyst in the system.

7. The catalytic distillation process according to claim 1, wherein the heterogeneous catalyst is a cation exchange resin.

8. The catalytic distillation process according to claim 1, wherein the heterogeneous catalyst comprises at least one metal oxide selected from the group of $Nb_2O_5$, $Al_2O_3$, $ZrO_2$, $TiO_2$, $Cr_2O_3$, $CrO_3$, $WO_3$, $W_2O_5$, $ZrW_xO_y$ wherein x is 2 and y is 0.5 to 8, $V_2O_5$, BeO, $MoO_3$, $Fe_2O_3$, $Ga_2O_3$, $La_2O_3$, ZnO and mixtures thereof.

9. The catalytic distillation process according to claim 1, wherein the heterogeneous catalyst contains an oxide selected from the group consisting of Fe, Ti, Zr, Hf, Sn, Si, Al and combinations thereof, and wherein the oxide has been treated by an acidic material, and wherein the acidic material is at least one of sulphate, tungstate, borate and molybdate.

10. The catalytic distillation process according to claim 1, wherein the solid acid catalysts with a Hammet acidity ($H_0$) less than 0 are amphoteric materials exhibiting basic sites.

11. The catalytic distillation process according to claim 1, wherein the catalyst is an amphoteric material exhibiting basic sites and includes any one or combination of MgO, $CeO_2$, $Al_2O_3$, $Fe_2O_3$ and $Cr_2O_3$.

12. A catalytic distillation process for production of performic acid, comprising:

feeding aqueous solutions of formic acid and an oxidizing agent under controlled flow rates into a catalytic distillation column containing one or more reaction zones, said one or more reaction zones including one or more heterogeneous catalysts immobilized in said one or more reactive zones, where said one or more heterogeneous catalysts are solid acid catalysts with Hammet acidity ($H_0$) less than 0;

said column being operated at sub atmospheric pressure and preselected temperature such that the oxidizing agent and formic acid are introduced in the one or more reaction zones and undergo a reaction to produce performic acid and reaction by products;

wherein performic acid enriched vapors flow upwards within the column and a liquid enriched in unreacted formic acid, unreacted oxidizing agent and reaction products descend downwards within the column; and withdrawing some or all of a performic acid enriched product stream from a condenser located at the top of the column to create a performic acid rich distillate product stream, for point of use application, optionally cooling the performic acid rich distillate product stream and optionally storing the performic acid rich distillate product stream, and optionally withdrawing a proportion of unreacted formic acid, unreacted oxidizing agent and reaction products from a reboiler located at the bottom of the column.

13. The catalytic distillation process according to claim 12, wherein the preselected temperature is in a range from about 0 to about 100° C.

14. The catalytic distillation process according to claim 12, wherein the preselected temperature in the one or more reaction zones containing the catalyst is in a range from about 15° C. to about 60° C.

15. The catalytic distillation process according to claim 12, wherein the preselected temperature in the one or more reaction zones containing the catalyst is in a range from about 20° C. to about 40° C.

16. The catalytic distillation process according to claim 12, wherein the oxidizing agent is hydrogen peroxide such that the hydrogen peroxide and formic acid mix in the one or more reaction zones and undergo the reaction (1) to produce performic acid and water as a reaction by product as follows

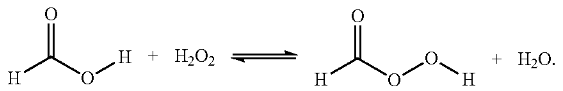

(1)

17. The catalytic distillation process according to claim 12, wherein the oxidizing agent is a compound which can produce hydrogen peroxide in situ via its chemical reaction with other compounds present in the system or from its interaction with the catalyst in the system.

18. The catalytic distillation process according claim 12, wherein the heterogeneous catalyst is a cation exchange resin.

19. The catalytic distillation process according to claim 12, wherein the heterogeneous catalyst comprises at least one metal oxide selected from the group of $Nb_2O_5$, $Al_2O_3$, $ZrO_2$, $TiO_2$, $Cr_2O_3$, $CrO_3$, $WO_3$, $W_2O_5$, $ZrW_xO_y$ wherein x is 2 and y is 0.5 to 8, $V_2O_5$, BeO, $MoO_3$, $Fe_2O_3$, $Ga_2O_3$, $La_2O_3$, ZnO and mixtures thereof.

20. The catalytic distillation process according to claim 1, wherein the heterogeneous catalyst contains an oxide selected from the group consisting of Fe, Ti, Zr, Hf, Sn, Si, Al and combinations thereof, and wherein the oxide has been treated by an acidic material, and wherein the acidic material is at least one of sulphate, tungstate, borate and molybdate.

21. The catalytic distillation process according to claim 12, wherein the heterogeneous catalyst is an amphoteric material exhibiting basic sites.

22. The catalytic distillation process according to claim 21, wherein the amphoteric material exhibiting basic sites includes any one or combination of MgO, $CeO_2$, $Al_2O_3$, $Fe_2O_3$ and $Cr_2O_3$.

23. The catalytic distillation process according to claim 12, further comprising returning a proportion of the performic acid rich distillate product stream into the top of the catalytic distillation column as liquid reflux, wherein a reflux rate is in a range from 0%, no reflux, to 99.9% returned to the column.

24. The catalytic distillation process according to claim 1, wherein the aqueous solutions of formic acid and the oxidizing agent are mixed together and then fed into the catalytic distillation column.

25. The catalytic distillation process according to claim 1, wherein the aqueous solutions of formic acid and the oxidizing agent are fed separately into the catalytic distillation column.

26. The catalytic distillation process according to claim 12, wherein the aqueous solutions of formic acid and the oxidizing agent are mixed together and then fed into the catalytic distillation column.

27. The catalytic distillation process according to claim 12, wherein the aqueous solutions of formic acid and the oxidizing agent are fed separately into the catalytic distillation column.

28. A catalytic distillation process for production of performic acid, comprising:

feeding aqueous solutions of formic acid and an oxidizing agent under controlled flow rates into a catalytic distillation column containing one or more reaction zones, said one or more reaction zones including one or more heterogeneous catalysts immobilized in said one or more reaction zones, where said one or more heterogeneous catalysts exhibit basic sites and have a Hammet basicity greater than 0;

said column being operated at sub atmospheric pressure and preselected temperature such that the oxidizing agent and formic acid are introduced to the one or more reaction zones and undergo a reaction to produce performic acid and reaction by-products;

wherein a performic acid enriched liquid product containing some unreacted oxidizing agent flows downwards within the column and wherein a vapor phase containing unreacted formic acid, some unreacted oxidizing agent and reaction products rise up within the column to a condenser located at the top of the column; and withdrawing the vapor phase containing the unreacted formic acid, some unreacted oxidizing agent and reaction products from a condenser located at the top of the column, and returning some or all of the condensed distillate back to the CD column as reflux, and withdrawing the performic acid enriched liquid product at or near the bottom of the column to create a performic acid rich bottoms product stream, optionally cooling the performic acid rich bottoms product stream and optionally storing the cooled performic acid rich bottoms product stream.

29. The catalytic distillation process according to claim 28, wherein the heterogeneous catalysts exhibiting basic sites and with Hammet basicity greater than zero are basic anion exchange resins.

30. The catalytic distillation process according to claim 28, wherein the heterogeneous catalysts exhibiting basic sites and with Hammet basicity greater than zero are amphoteric materials.

31. A catalytic distillation process for production of performic acid, comprising:

feeding aqueous solutions of formic acid and an oxidizing agent under controlled flow rates into a catalytic distillation column containing one or more reaction zones, said one or more reaction zones including one or more heterogeneous catalysts immobilized in said one or more reactive zones, where said on or more heterogeneous catalysts exhibit basic sites and have a Hammet basicity greater than 0;

said column being operated at sub atmospheric pressure and preselected temperature such that the oxidizing agent and formic acid are introduced in the one or more reaction zones and undergo a reaction to produce performic acid and reaction by products;

wherein performic acid enriched vapors flow upwards within the column and a liquid enriched in unreacted formic acid, unreacted oxidizing agent and reaction products descend downwards within the column; and withdrawing some or all of a performic acid enriched product stream from a condenser located at the top of the column to create a performic acid rich distillate product stream, for point of use application, optionally cooling the performic acid rich distillate product stream and optionally storing the performic acid rich distillate product stream, and optionally withdrawing a proportion of unreacted formic acid, unreacted oxidizing agent and reaction products from a reboiler located at the bottom of the column.

32. The catalytic distillation process according to claim 31, wherein the heterogeneous catalysts exhibiting basic sites and with Hammet basicity greater than zero are basic anion exchange resins.

33. The catalytic distillation process according to claim 31, wherein the heterogeneous catalysts exhibiting basic sites and with Hammet basicity greater than zero are amphoteric materials.

34. The catalytic distillation process according to claim 9, wherein the one or more heterogeneous catalysts is selected from:

a) the group consisting of $SO_4/SnO_2$, $SO_4/ZrO_2$, $SO_4/HfO_2$, $SO_4/TiO_2$, $SO_4/Al_2O_3$, $SO_4/Fe_2O_3$ and $SO_4/SiO_2$, formed by exposure of Fe, Ti, Zr, Hf, Sn, Si and Al to acidic sulphate;

b) the group consisting of $WO_3/ZrO_2$, $WO_3/TiO_2$ and $WO_3/Fe_2O_3$, formed by exposure of Fe, Ti and Zr to acidic tungstate;

c) $MoO_3/ZrO_2$, formed by exposure of Zr to acidic molybdate;

d) $B_2O_3/ZrO_2$, formed by exposure of Zr to acidic borate; and any combination of the heterogeneous catalysts listed in a), b) and c).

35. The catalytic distillation process according to claim 20, wherein the one or more heterogeneous catalysts is selected from a) the group consisting of $SO_4/SnO_2$, $SO_4/ZrO_2$, $SO_4/HfO_2$, $SO_4/TiO_2$, $SO_4/Al_2O_3$, $SO_4/Fe_2O_3$ and $SO_4/SiO_2$, formed by exposure of Fe, Ti, Zr, Hf, Sn, Si and Al to acidic sulphate;

b) the group consisting of $WO_3/ZrO_2$, $WO_3/TiO_2$ and $WO_3/Fe_2O_3$, formed by exposure of Fe, Ti and Zr to acidic tungstate;

c) $MoO_3/ZrO_2$, formed by exposure of Zr to acidic molybdate;

d) $B_2O_3/ZrO_2$, formed by exposure of Zr to acidic borate; and any combination of the heterogeneous catalysts listed in a), b) and c).

36. The catalytic distillation process according to claim 1, for production of performic acid for use in wastewater treatment.

37. The catalytic distillation process according to claim 1, for production of performic acid for use in industrial effluent treatment, food processing equipment, and medical device disinfection.

38. The catalytic distillation process according to claim 12, for production of performic acid for use in wastewater treatment.

39. The catalytic distillation process according to claim 12, for production of performic acid for use in industrial effluent treatment, food processing equipment, and medical device disinfection.

40. The catalytic distillation process according to claim 28, for production of performic acid for use in wastewater treatment.

41. The catalytic distillation process according to claim 28, for production of performic acid for use in industrial effluent treatment, food processing equipment, and medical device disinfection.

42. The catalytic distillation process according to claim 31, for production of performic acid for use in wastewater treatment.

43. The catalytic distillation process according to claim 31, for production of performic acid for use in industrial effluent treatment, food processing equipment, and medical device disinfection.

44. The catalytic distillation process according to claim 1 wherein the sub atmospheric pressure is in a range from about $1\times10^{-6}$ psia to about 14.7 psia.

45. The catalytic distillation process according to claim 1, wherein the pressure is in a range from about 0.1 to about 3 psia.

46. The catalytic distillation process according to claim 1, wherein the pressure is in a range from about 0.3 to about 1.1 psia.

47. The catalytic distillation process according to claim 12, wherein the sub atmospheric pressure is in a range from about $1\times10^{-6}$ psia to about 14.7 psia.

48. The catalytic distillation process according to claim 12, wherein the pressure is in a range from about 0.1 to about 3 psia.

49. The catalytic distillation process according to claim 12, wherein the pressure is in a range from about 0.3 to about 1.1 psia.

50. The catalytic distillation process according to claim 28, wherein the sub atmospheric pressure is in a range from about $1\times10^{-6}$ psia to about 14.7 psia.

51. The catalytic distillation process according to claim 28, wherein the pressure is in a range from about 0.1 to about 3 psia.

52. The catalytic distillation process according to claim 28, wherein the pressure is in a range from about 0.3 to about 1.1 psia.

53. The catalytic distillation process according to claim 31, wherein the sub atmospheric pressure is in a range from about $1\times10^{-6}$ psia to about 14.7 psia.

54. The catalytic distillation process according to claim 31, wherein the pressure is in a range from about 0.1 to about 3 psia.

55. The catalytic distillation process according to claim 31, wherein the pressure is in a range from about 0.3 to about 1.1 psia.

56. The catalytic distillation process according to claim 28, wherein the preselected temperature in the one or more reaction zones containing the catalyst is in a range from about 20° C. to about 40° C.

57. The catalytic distillation process according to claim 31, wherein the preselected temperature in the one or more reaction zones containing the catalyst is in a range from about 20° C. to about 40° C.

* * * * *